United States Patent
Soetebier et al.

(10) Patent No.: US 11,390,066 B2
(45) Date of Patent: Jul. 19, 2022

(54) METHOD FOR CONTROLLING THE CURING DEGREE OF AT LEAST ONE AT LEAST PARTIALLY CURED INK AND/OR VARNISH PRINTED ON A SUBSTRATE

(71) Applicant: HUBERGROUP DEUTSCHLAND GMBH, Kirchheim-Heimstetten (DE)

(72) Inventors: Carina Soetebier, Munich (DE); Alexander Blasek, Heldenfingen (DE); Christian Kaindl, Pfaffenhofen (DE); Taner Bicer, Grafing (DE)

(73) Assignee: HUBERGROUP DEUTSCHLAND GMBH, Kirchheim-Heimstetten (DE)

( * ) Notice: Subject to any disclaimer, the term of this patent is extended or adjusted under 35 U.S.C. 154(b) by 0 days.

(21) Appl. No.: 16/964,282

(22) PCT Filed: Nov. 8, 2019

(86) PCT No.: PCT/EP2019/080742
§ 371 (c)(1),
(2) Date: Jul. 23, 2020

(87) PCT Pub. No.: WO2020/187431
PCT Pub. Date: Sep. 24, 2020

(65) Prior Publication Data
US 2021/0229417 A1  Jul. 29, 2021

(30) Foreign Application Priority Data

Mar. 15, 2019  (EP) .................... 19163236

(51) Int. Cl.
*B41F 23/04*   (2006.01)
*G01N 21/31*   (2006.01)
*G01N 33/32*   (2006.01)

(52) U.S. Cl.
CPC ...... *B41F 23/0453* (2013.01); *B41F 23/0409* (2013.01); *G01N 21/31* (2013.01); *G01N 33/32* (2013.01)

(58) Field of Classification Search
CPC . B41F 23/0453; B41F 23/0409; G01N 21/31; G01N 3/32; G01N 21/33
See application file for complete search history.

(56) References Cited

U.S. PATENT DOCUMENTS 5,937,761 A  8/1999 Buschmann et al.
7,043,326 B2  5/2006 Neubauer et al.
(Continued)

FOREIGN PATENT DOCUMENTS

WO  9723550 A1  7/1997
WO  2009153045 A1  12/2009
WO  2018189248 A1  10/2018

OTHER PUBLICATIONS

Extended European Search Report issued by the European Patent Office dated Jul. 5, 2019, in priority application No. EP 19163236 (for information only, not prior art).
(Continued)

*Primary Examiner* — Leslie J Evanisko
*Assistant Examiner* — Leo T Hinze
(74) *Attorney, Agent, or Firm* — Lelkes IP; Robert Lelkes

(57) ABSTRACT

The present invention relates to a method for controlling the curing degree of at least one at least partially cured ink and/or varnish printed on a substrate, which comprises cutting at least one sample from an area of the printed substrate, placing and incubating it in a solvent, in which at least one of the at least one extractable compound is soluble, and removing it from the solvent to obtain a solvent extract; quantitatively measuring a spectroscopic characteristic of the solvent extract; comparing the measured numeric value of the spectroscopic characteristic with a reference value of
(Continued)

the spectroscopic characteristic for the same area of the printed substrate; and outputting a result, wherein the reference value of the spectroscopic characteristic for the same area of the printed substrate has been obtained by the use of an empirical model.

14 Claims, 1 Drawing Sheet

(56) References Cited

U.S. PATENT DOCUMENTS

| 7,323,693 | B2 | 1/2008 | Sanuki et al. | |
|---|---|---|---|---|
| 2004/0180226 | A1* | 9/2004 | Chatterjee | C08F 222/102 |
| | | | | 428/458 |
| 2021/0131965 | A1* | 5/2021 | Luschtinetz | G01N 21/31 |

OTHER PUBLICATIONS

George E. P. Box, Norman R. Draper, "Empirical Model-Building and Response Surfaces" (Wiley, 1987) ISBN-13: 978-0471810339, pp. 10-14.

George E.P. Box, J. Stuart Hunter, William G. Hunter, "Statistics for Experimenters", 2nd ed., (Wiley, 2005) ISBN-13: 978-0471718130, pp. 235-245.

International Search Report (ISR) and Written Opinion mailed by the European Patent Office dated Feb. 3, 2020, in International Patent Application No. PCT/EP2019/080742 (for information only, not prior art).

Peter Goos, Bradley Jones, "Optimal Design of Experiments—A Case Study Approach" (Wiley 2011) ISBN-13: 978-0470744611, pp. 69-70, 95, 135-136.

* cited by examiner

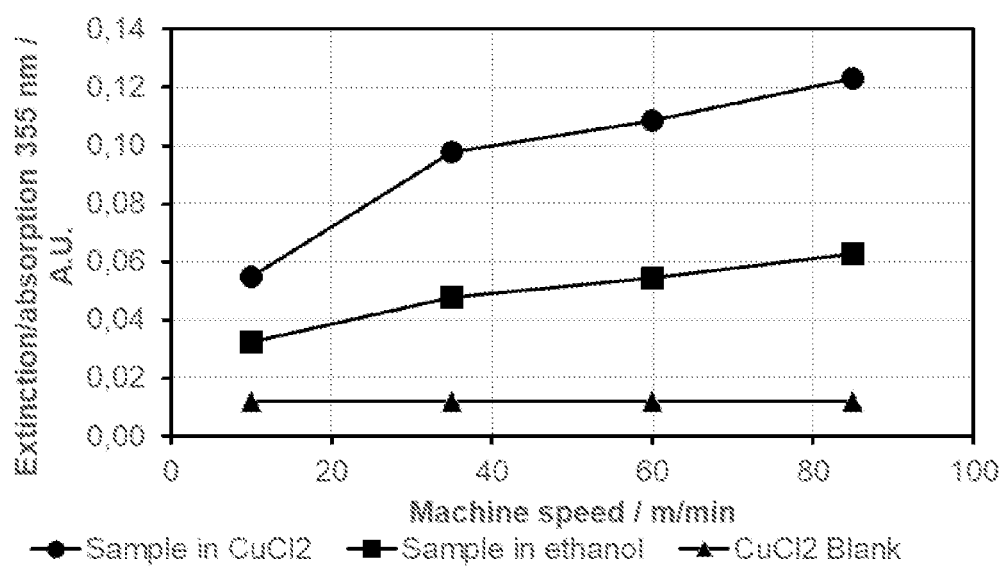

METHOD FOR CONTROLLING THE CURING DEGREE OF AT LEAST ONE AT LEAST PARTIALLY CURED INK AND/OR VARNISH PRINTED ON A SUBSTRATE

CROSS-REFERENCE TO RELATED APPLICATIONS

This is the U.S. national phase of international patent application no. PCT/EP2019/080742 filed on Nov. 8, 2019, which claims priority based on European patent application no. 19163236 filed on Mar. 15, 2019.

BACKGROUND OF THE INVENTION

The present invention relates to a method for controlling the curing degree of at least one at least partially cured ink and/or varnish applied on a substrate.

Most of the commercially distributed consumer products are enclosed in a packing, which is often made of paper, cardboard, plastic foil, fabric, metal foil or the like, so as to cover, protect and/or preserve the product. Such packagings are predominantly printed with an ink and/or varnish, in order to improve the optical appearance of the packing and in order to present information about the enclosed product. Prominent examples therefore are printed food packagings, which present information about the enclosed product, such as about the price, about the size, about the composition, about the nutrients, about the storage life, and about the country of origin of the product.

A plurality of printing techniques is available to print a substrate with an ink and/or varnish, such as offset printing, flexographic printing, digital printing, intaglio printing and many others. Most of these printing processes are continuous processes, such as web offset, flexographic printing, gravure or intaglio printing, or semi-continuous processes, such as sheet-fed offset. It is essential to assure during the printing process that a sufficiently high curing degree of the ink and/or varnish is obtained during a predetermined time so as to assure that the printed substrate is abrasion resistant at the time, when its surface firstly comes into contact with another article, such as when in the sheet-fed offset printing process a further sheet is arranged onto the printed sheet, in order to avoid that the ink and/or varnish is abraded. Proper curing is especially required if the printed sheets are further processed to form e.g. folding cartons or brochures; in other words, the printed substrate needs to be suitable for post-press processes without the print being affected or destroyed. However, it is often preferred that the curing degree is not significantly higher than necessary, because then unnecessary energy is consumed during the printing process. The curing degree of an ink/varnish depends on a plurality of parameters, such as from the composition of the ink and/or varnish, the nature and amount of included binder, photoinitiator(s), synergist(s), additives, fillers, solvents, reactive diluents, and the like, the thickness of the ink/varnish layer on the substrate, the ink/varnish coverage, the applied ink gram mage, the kind of substrate, the printing machine speed, and many other parameters.

Another important aspect of adjusting a sufficiently high curing degree of the ink and/or varnish during the printing process is to avoid that the migration potential of the ink and/or varnish after printing is too high. For instance, an important requirement of a printed food packing is that a contamination of the product with ingredients of the packing and in particular from the ink and/or varnish, with which the packing is printed, is reliably avoided. Such a contamination cannot only harm the quality of the product, such as the taste and smell, but may be even poison the product and the consumer. This is in particular relevant for primary food packagings, which come with their unprinted inner side into direct contact with the enclosed product; in contrast to secondary food packagings, which enclose a further packing, in which the product is contained. Common printing inks and varnishes contain ingredients with a low molecular weight, which thus have a high migration potential and are able to diffuse out of the cured ink or cured varnish, respectively, and through the packing. This applies in particular for energy curing printing inks and varnishes, such as UV curing printing inks and varnishes, i.e. printing inks and varnishes, for which the curing is initiated by UV light. Such printing inks and varnishes include among other compounds photoinitiators, monomers and oligomers, which have a quite low molecular weight and which are thus characterized by a high migration potential. Thus, a sufficiently high curing degree has to be assured so that at least essentially all of the photoinitiators, monomers, and oligomers are converted.

Several methods to determine the curing degree are known, such as those described for example in U.S. Pat. No. 7,323,693 B2, in U.S. Pat. No. 7,043,326 B2, in WO 2009/153045 A1 and in WO 2018/189248 A1. However, in particular the determination of the curing degree of energy curing inks and varnishes is still a challenge. Another challenge is the control of the curing degree during the printing process and particularly during a printing process, in which an energy curing ink and/or varnish is used. Usually, a printer adjusts the power of the UV lamps, the machine speed of an e.g. web-offset printing machine, the number of UV lamps, their position (interdeck or end-of-press dryer), and the type of UV lamp based on his experience. However, this does of course not reliably assure that any part of the produced printed substrate has an optimal curing degree. Moreover, the curing degree may change during the printing process, so that determining the curing degree of one sample produced, for instance during a sheet-fed offset process at a first point of time, does not necessarily mean that the curing degree of another sample, printed before or after the first point of time, is the same. It is of course possible to adjust the process parameters for instance of a sheet-fed offset process using UV curing inks and/or varnishes so that an excess of UV energy is applied to the printed substrate, that the machine speed is comparably slow and multiple UV lamps are used so as to adjust a curing degree being as high as possible.

However, the curing degree may then be even higher than necessary, so that a high amount of the applied UV energy is wasted and the machine speed is slower than necessary, thus decreasing the printing efficiency and increasing energy costs.

In view of all this, the object underlying the present invention is to provide a method for controlling the curing degree of at least one at least partially cured ink and/or varnish printed on a substrate and in particular of at least one at least partially cured energy curing ink and/or varnish printed on a substrate, which allows to reliably adjust the required curing degree of the at least one ink and/or varnish of the printed substrate assuring a high printing quality, and which further allows to achieve a minimal energy consumption and a maximal possible machine speed during the printing process, but which is nevertheless easy, fast, and cost-efficiently to perform.

BRIEF SUMMARY OF THE INVENTION

In accordance with the present invention, this objective is achieved by providing a method for controlling the curing degree of at least one at least partially cured ink and/or varnish printed on a substrate, which comprises the following steps:

a) providing a substrate, which is printed with the at least one at least partially cured ink and/or at least partially cured varnish, wherein the at least one at least partially cured ink and/or at least partially cured varnish comprises at least one extractable compound, b) cutting at least one sample from an area of the printed substrate provided in step a), placing the at least one sample in a solvent, in which at least one of the at least one extractable compound is soluble, incubating the solvent with the at least one sample placed therein for at least 10 seconds and removing the at least one sample from the solvent to obtain a solvent extract, c) quantitatively measuring a spectroscopic characteristic of the solvent extract at at least one wavelength between 190 and 4,000 nm, at which at least one of the at least one extractable compound absorbs or emits radiation, so as to obtain a measured numeric value of the spectroscopic characteristic, d) comparing the measured numeric value of the spectroscopic characteristic measured in step c) with a reference value of the spectroscopic characteristic for the same area of the printed substrate, from which the at least one sample has been cut out in step b), and e) outputting a result, wherein the reference value of the spectroscopic characteristic for the same area of the printed substrate, from which the at least one sample has been cut out in step b), has been obtained by the use of an empirical model.

BRIEF DESCRIPTION OF THE DRAWING

The FIGURE shows data plots of extinction/absorption values at 355 nm versus machine speed in meters per minute based on data obtained in Example 2 below.

DETAILED DESCRIPTION OF THE INVENTION

This solution is based on the surprising finding that by making use of a reference value obtained in the aforementioned manner with an empirical model, for any specific printing system, i.e. for any specific combination of used printing machine, used printing process parameters (such as printing speed, applied UV intensity and/or dosage and/or irradiance, drying temperature, and the like), applied inks and/or varnishes, applied substrate, adjusted grammage, adjusted ink/varnish coverage, and the like, a reliable control of the curing degree of the applied inks and varnishes on the printed substrate is possible by simply comparing the numeric value measured in step c) with the reference value. More specifically, the absolute value of the difference of the numeric value measured in step c) and the reference value is a reliable parameter for the curing degree of the sample of this specific printing system. In addition, the curing degree actually determined for the sample allows a reliable feedback to the printer, whether the printing process may be continued without any amendment, since the curing degree is in the optimal range, or whether any amendment of the printing process is necessary so as to increase the curing degree of the ink and/or varnish, or whether any amendment of the printing process is advisable so as to increase the printing efficiency by increasing the machine speed and/or to decrease the operational costs, such as the energy costs, by decreasing the curing degree of the ink and/or varnish from a value being higher than necessary to a value being high enough for the purpose, e.g. by reducing the intensity of the UV lamp. A particular advantage of the method in accordance with the present invention is that it is universally applicable and in particular essentially not limited with regard to the kind and material of the substrate, with regard to the kind and composition of the ink and/or varnish, with regard to the printing process, with regard to the parameters used in the printing process, with regard to the curing method and with regard to the curing parameters. All in all, the method in accordance with the present invention allows to reliably control the curing degree of any at least partially cured ink and/or varnish printed on a substrate irrespective from the composition of the ink/varnish, from the printing process, from the parameters used in the printing processes and from the substrate. Since the method in accordance with the present invention requires nothing more than cutting a sample from the printed substrate, placing it in a solvent and measuring a spectroscopic characteristic of the solvent extract obtained thereby, such as the extinction/absorption value at 310 nm, the method is easy, fast, and cost-efficiently to perform.

The reference value of the spectroscopic characteristic for the same area of the printed substrate, from which the at least one sample has been cut out in step b), which has been obtained by the use of an empirical model, preferably is determined so that it represents the curing degree which is sufficiently high for the specific printing process to ensure a proper post-press processing. Therefore, it is preferably defined and adjusted according to the requirements or specifications of the actual print job. The requirements or specifications of the actual print job may be defined by the user of the method. These specifications can be for instance for food-packaging applications the compliance with legal requirements which means that the reference value of the spectroscopic characteristic, such as the extinction value, needs to correspond to maximum allowed migration values of migrating compounds. When the substrate is e.g. folded or bended in the post-press process the requirement is different or even an additional one. In this case the ink film must remain whole without breaks or cracks in the folding or bending area. In such cases the reference value can in addition be correlated to e.g. FT-IR spectrometry or migration results. Other examples for these specifications of the actual print job may be the scratch resistance of the printed product or similar properties.

Area means a location of the printed substrate, such as a dot or rectangular having a certain dimension, such as of 4 $cm^2$. In accordance with the present invention, the reference value of the spectroscopic characteristic is for the same area of the printed substrate, from which the at least one sample has been cut out in step b), i.e. the reference value is for the same location, such as a dot with a diameter of 2 cm at a precise location of the printed substrate, which has been cut out in step b) by the user.

Empirical modelling means in accordance with the present invention, as generally defined in this field, any kind of (computer) approximation of empirical observations by a mathematical function. More specifically, empirical modelling is a generic term for activities that create models by observation and experiment. Empirical models are in detail described and defined for instance by George E. P. Box, Norman R. Draper in "Empirical Model-Building and Response Surfaces", Wiley 1987 and by Peter Goos, Bradley Jones in "Optimal Design of Experiments—A Case Study Approach", Wiley 2011.

Method for controlling the curing degree of at least one at least partially cured ink and/or varnish printed on a substrate in accordance with the present invention means that any system comprising at least one at least partially cured ink and/or varnish is printed on a substrate. For instance, a primer may be arranged between the substrate and the at least one at least partially cured ink and/or varnish. Also, one or more lacquers may be applied onto the at least one at least partially cured ink and/or varnish, such as a water based lacquer, an oil based varnish, a solvent based lacquer and the like.

The method for controlling the curing degree of at least one at least partially cured ink and/or varnish printed on a substrate in accordance with the present invention is preferably (also) a method for the quality control of the curing degree of at least one at least partially cured ink and/or varnish printed on a substrate.

The method is particularly suitable, but not restricted to continuous printing processes, such as web offset, flexographic printing, gravure printing, and the like as well as to semi-continuous printing processes, such as sheet-fed offset and the like.

In accordance with the present invention the measured numeric value of the spectroscopic characteristic measured in step c) is compared with a reference value of the spectroscopic characteristic for the same area of the printed substrate, from which the at least one sample has been cut out in step b), wherein the reference value of the spectroscopic characteristic for the same area of the printed substrate, from which the at least one sample has been cut out in step b), has been obtained by the use of an empirical model. Preferably, not only one reference value has been obtained only for one area of the printed substrate. Rather, it is preferred that more than one reference value has been obtained by an empirical model for different areas of the printed substrate. In particular, it is preferred that the total area of the printed substrate is subdivided in a plurality of (partial) areas, such as (partial) areas of each 4 cm$^2$, wherein each of the (partial) areas preferably has the same size as the sample to be cut out in step b), and wherein a reference value of the spectroscopic characteristic to be measured in step c) is obtained by the empirical method for each of the (partial) areas. This allows the user of the method to arbitrarily decide, from which part of the printed substrate the one or more samples are cut out in step b).

In accordance with a preferred embodiment of the present invention, the reference value of the spectroscopic characteristic for the same area of the printed substrate, from which the at least one sample has been cut out in step b), has been obtained by the use of an empirical model, which is selected from the group consisting of linear models, of second order models, and of higher order models. A linear model includes only terms that are linear in the settings of the experimental factors or parameters, respectively, whereas a second order model includes interaction terms and quadratic terms as well.

It is proposed in a further development of the idea of the present invention that the empirical model used in the method has been obtained by making use of a design of experiments. Design of experiment is a methodology for systematically planning and evaluating of experiments. More specifically, a design of experiments is a very efficient methodology for determining the functional relationship of influencing parameters and of the results. Good results are in particular obtained, when the design of experiments is selected from the group consisting of optimal designs of experiments, full factorial designs of experiments, fractional factorial designs of experiments, centrally composed experimental designs and combinations thereof. A full factorial design comprises all possible combinations of all settings of all factors or parameters, respectively. More specifically, a full factorial experiment is an experiment whose design consists of two or more factors, each with discrete possible values or levels, and whose experimental units take on all possible combinations of these levels across all such factors. Such an experiment allows the investigator to study the effect of each factor on the response variable, as well as the effects of interactions between factors on the response variable. Optimal designs usually comprise a subset of a full factorial design, which is for example selected by means of an algorithm that maximizes the so-called information matrix (D-optimal). Optimal designs are optimal with respect to some statistical criterion. A non-optimal design requires a greater number of experimental runs to estimate the parameters with the same precision as an optimal design. Fractional factorial designs are experimental designs consisting of a carefully chosen subset, i.e. fraction, of the experimental runs of a full factorial design. The subset is chosen so as to exploit the sparsity-of-effects principle to expose information about the most important features of the problem studied, while using a fraction of the effort of a full factorial design in terms of experimental runs and resources. A central composite design is an experimental design for building a second order model for the response variable without needing to use a complete three-level factorial experiment. Other optimality criteria are described in statistical textbooks. Fractional factorial designs use half of the settings of a full factorial design, a quarter, an eighth or even a smaller part, selected in a way that the vectors of the design matrix are orthogonal. For more details see for example "Statistics for Experimenters", George E. P. Box, J. Stuart Hunter, William G. Hunter, ISBN-13: 978-0471718130.

Preferably, the design of experiments used for obtaining the reference value(s) is a full factorial design of experiments, a fractional factorial design of experiments or an optimal design of experiments, such as an A-optimal design of experiments, a D-optimal design of experiments, an E-optimal design of experiments or a G-optimal design of experiments.

More preferably, the empirical model has been obtained by making use of the results of a D-optimal design of experiments. D-optimal designs are very flexible and can be adopted to a large variety of situations. Moreover, they allow to use experimental capacity in a very efficient way.

Most preferably, the reference value of the spectroscopic characteristic for the same area of the printed substrate, from which the at least one sample has been cut out in step b), has been obtained by the use of a second order empirical model obtained by making use of the results of a D-optimal design of experiments.

It is the core of a design of experiments that one or more parameters are varied during the set of experiments so as to determine the functional relationship of influencing parameters. Preferably, the empirical model has been obtained in the method in accordance with the present invention by making use of the results of a plurality of experiments, in which the spectroscopic characteristic measured in step c) has been measured for an area of a printed substrate, wherein the plurality of experiments has been made by printing at least one ink and/or varnish onto the substrate, wherein one or more of the printing parameters have been varied in the individual experiments.

Good results are in particular obtained, when at least one parameter has been varied in the experiments, which is selected from the group consisting of ink coverage of each ink, gram mage of each ink, density of each ink, type of substrate, printing speed, UV lamp type, UV lamp intensity, UV lamp dosage, extraction time, and arbitrary combinations of two or more of the aforementioned parameters.

Grammage of ink means the amount of dry ink that is applied to a defined area of substrate, either directly or indirectly by means of a printer.

It is suggested in a further development of the idea of the present invention that at least two parameters, preferably at least three parameters, more preferably at least four parameters, even more preferably at least five parameters, still more preferably at least six parameters, and most preferably at least eight parameters, such as from the aforementioned parameters, have been varied in the experiments proposed by the design of experiments.

In a particular preferred embodiment of the present invention, the reference value of the spectroscopic characteristic for the same area of the printed substrate, from which the at least one sample has been cut out in step b), has been obtained by the use of a second order empirical model obtained by making use of the results of a D-optimal design of experiments, wherein in the D-optimal design of experiments at least one of the parameters selected from the group consisting of ink coverage of each ink, grammage of each ink, density of each ink, type of substrate, printing speed, UV lamp type, UV lamp intensity, UV lamp dosage, extraction time, and arbitrary combinations of two or more of the aforementioned parameters has been varied, wherein the other parameters were preferably as for printing the substrate provided in step a).

An example for a second order empirical model is the following equation:

$$\eta = \beta_0 + \sum_{i=1}^{n} \beta_i \cdot x_i + \sum_{i \leq j}^{n} \sum_{j}^{n} \beta_{ij} \cdot x_i \cdot x_j$$

in which
η is the spectroscopic characteristic measured in step c), such as the extinction/absorption of the solvent extract at 310 nm,
$\beta_0$, $\beta_i$, $\beta_{ij}$ are the coefficients of the single parameters varied during the plurality of experiments as calculate by the statistics program, and
$x_i$, $x_j$ are the settings of the different parameters varied during the plurality of experiments.

For instance, for a printed substrate obtained with sheet-fed offset a D-optimal design of experiments for a defined ink series may be made, in which the parameters ink coverage of each ink, grammage and/or density of each ink, type of substrate, printing speed, UV lamp type, UV lamp intensity, UV lamp dosage, sample area, and extraction time are varied.

For example, in such a set of experiments, the following parameters may be varied as follows:
Substrate: coated paper/cardboard, uncoated paper/cardboard, plastic film, aluminum foil or a metal sheet,
Grammage: between 0.2 and 2.5 g/m², for instance in 0.2 g/m² steps,
Color density: between 0.2-2.0, for instance in 0.2 steps
Ink coverage of each ink: 0%, 20%, 40%, 60%, 80%, 100%
Printing speed: 10.000-16.000 sheets/hour or 10-400 m/min, for instance in 1.000 sheets/hour steps
UV lamp type: Hg-UV, HUV (iron-doped UV lamps), and LED
UV lamp intensity: 0-100%, for instance in 20% steps,
UV lamp dosage: 5-700 mJ/cm², for instance in 10 mJ/cm² steps,
Sample area: 4-20 cm², for instance in 2 cm² steps,
Extraction time: 2, 5, and 8 min, for instance in 1 min steps.

For evaluating these experiments, the spectroscopic characteristic, preferably the absorption of UV light in the range of 190 to 450 nm, and more preferably at the maximum wavelength of the extractable compound of the respective ink series, is measured for each of a plurality of solvent extracts, wherein each solvent extract is obtained as described above for a sample having been cut out of each of the printed substrates obtained in experiments performed in the set of experiments by varying the aforementioned parameters. An empirical model is developed using a statistics program, like Cam Line Cornerstone 7, Statgraphics Centurion 18 or Minitab 18, that allows to describe the relation between the spectroscopic characteristic and these parameters. As set out above, the model used is preferably an empirical model of second order. Details how such models can be developed and optimized are described e.g. in "Statistics for Experimenters", George E. P. Box, J. Stuart Hunter, William G. Hunter, ISBN-13: 978-0471718130. The obtained empirical model contains reference values of the spectroscopic characteristic for all ink combinations and grammages as well as print conditions, for one defined ink series. For a different ink series, a different model needs to be developed.

The empirical model allows then to calculate for a certain printing process, e.g. an actual printing job of a printer, in which a certain pattern shall be printed with specific ink(s) and/or varnish(es) (such as UV curing ink(s)) of a specific ink series with a specific printing process (such as sheet-fed offset) with specific printing parameters (such as certain UV lamps) on a specific substrate, for each area of the pattern a reference value for the spectroscopic characteristic, if the required data, such those selected from the group consisting of printing process, used ink(s) and/or varnish(es), used UV lamps, ink coverage of each ink, grammage of each ink, density of each ink, type of substrate, printing speed, UV lamp type, UV lamp intensity, UV lamp dosage, extraction time, and arbitrary combinations of two or more of the aforementioned parameters, are entered into the empirical model. For this purpose, at least the ink series, ink composition, ink coverage, and value for the spectroscopic characteristic (such as extinction/absorption value) should be entered into the empirical model. The other aforementioned parameters may be entered optionally. However, it is preferred that also one or more and most preferably all of the other aforementioned parameters are entered into the empirical model.

All kinds of UV lamps may be used, such as a mercury vapor lamp, which may be or may not be iron-, gallium/indium- or lead doped.

Although it is possible to thereby calculate reference values for every area of the pattern, when the required data are entered into the statistics program, this is not mandatorily required. Rather, it is sufficient that the printer selects one area of the pattern of the printed substrate to be produced during the printing process and enters into the empirical model the required data for this area only.

Consequently, the reference value of the spectroscopic characteristic for the same area of the printed substrate, from which the at least one sample has been cut out in step b), may be obtained in accordance with a preferred embodiment of the present invention by performing the following steps:

i) generating a design of experiments using a statistics program designed for calculating an empirical model so as to propose a plurality of experiments, wherein in at least some, preferably in most or in each of these experiments at least one specific at least partially cured ink and/or at least partially cured varnish is printed under specific conditions with specific printing parameters onto a specific substrate, wherein most of these experiments differs from all other experiments of the plurality of experiments in at least one parameter, ii) performing the plurality of experiments proposed in step i), wherein for each of the experiments at least one sample is cut out from a specific area of the printed substrate, which is placed in a solvent, in which at least one of the at least one extractable compound is soluble, the solvent with the at least one sample placed therein is incubated for at least 10 seconds, the at least one sample is removed from the solvent to obtain a solvent extract, a spectroscopic characteristic of the solvent extract is quantitatively measured at at least one wavelength between 190 and 4,000 nm, at which at least one of the at least one extractable compound absorbs or emits radiation, so as to obtain a measured numeric value of the spectroscopic characteristic, iii) entering the numeric values of the spectroscopic characteristic measured in step ii) into the statistics program, iv) allowing the statistics program to calculate an empirical model, v) entering the numeric value of the spectroscopic characteristic measured in step c) as well as the parameters of the printing process, with which the substrate was printed in step a) into the statistics program and vi) allowing the statistics program to calculate the reference value of the spectroscopic characteristic for the same area of the printed substrate, from which the at least one sample has been cut out in step b).

As set out above, the reference value of the spectroscopic characteristic for the same area of the printed substrate, from which the at least one sample has been cut out in step b), is preferably determined so that it represents the curing degree which is sufficiently high for the specific printing process to ensure a proper post-press processing. Therefore, the user or provider of the statistics program may enter into the statistics program the characteristics for a sufficiently high curing degree for his actual printing job. For example, the user may enter into the statistics program a curing degree being sufficient so that the migration value of migrating compounds in a printed food-packaging is as required, or so that the scratch resistance of the printed product is as required.

As further set out above, the method in accordance with the present invention allows to reliably determine for any printing system the curing degree of the at least partially cured ink and/or at least partially cured varnish and to give from this determined curing degree a reliable feedback to the printer, whether the printing process may be continued without any amendment, since the curing degree is the optimal range, or whether any amendment of the printing process is necessary so as to increase the curing degree of the ink and/or varnish, or whether any amendment of the printing process is advisable so as to increase the printing efficiency by increasing the machine speed and/or to decrease the operational costs, such as the energy costs (e.g. by reducing the intensity of the UV lamp), by decreasing the curing degree of the ink and/or varnish from a value being higher than necessary to a value being high enough for the purpose. More specifically, it is preferred that the result being output in step e) from the comparison of the measured numeric value of the spectroscopic characteristic measured in step c) with the reference value is that:

i) the curing degree is sufficient, if the difference between the numeric value of the spectroscopic characteristic measured in step c) and the respective reference value is between a predetermined lower and an upper threshold, such as between −25% and +25%, preferably between −20% and +20%, more preferably between −15% and +15%, even more preferably between −10% and +10%, and most preferably between −5% and +5%, so that no amendment of the printing process is necessary, ii) the curing degree is too low, if the difference between the numeric value of the spectroscopic characteristic measured in step c) from the respective reference value is less than a predetermined lower threshold, such as less than −25%, preferably less than −20%, more preferably less than −15%, even more preferably less than −10%, and most preferably less than −5%, so that an amendment of the printing process is necessary, or iii) the curing degree is higher than necessary, if the difference between the numeric value of the spectroscopic characteristic measured in step c) from the respective reference value is more than a predetermined higher threshold, such as more than +25%, preferably more than +20%, more preferably more than +15%, even more preferably more than +10%, and most preferably more than +5%, so that an amendment is advisable.

In particular, when the result being output in step e) is that the curing degree is too low, in step e) an information is or may be given to the user or printer, respectively, with which amendment(s) of the printing process the curing degree may be increased to a satisfactory value. For instance, the information may comprise at least one of:

i) displaying the extent of how much the machine speed has to be reduced, if the printing process is a continuous process, such as web offset, flexographic printing, gravure printing or intaglio printing, or a semi-continuous process, such as sheet-fed offset process, and/or ii) displaying the extent of how much the lamp power for curing the at least one printing ink and/or varnish has to be increased, if the curing is supported by irradiation, and/or iii) displaying the number of additional lamps being necessary for curing the at least one printing ink and/or varnish, if the curing is supported by irradiation, and/or iv) displaying the extent of how much the temperature during the curing has to be increased.

Likewise thereto, when the result being output in step e) is that the curing degree is higher than necessary, in step e) an information may be given to the user or printer, respectively, with which amendment(s) of the printing process the curing degree may be decreased to a still satisfactory value. For example, the information may comprise at least one of:

i) displaying the extent of how much the machine speed has to be increased, if the printing process is a continuous process, such as web offset, flexographic printing, gravure printing or intaglio printing, or a semi-continuous process, such as sheet-fed offset process, and/or ii) displaying the extent of how much the lamp power for curing the at least one printing ink and/or varnish has to be reduced, if the curing is supported by irradiation, and/or iii) displaying the number of lamps, which have to be switched off, if the curing is supported by irradiation, and/or iv) displaying the extent of how much the temperature during the curing has to be reduced, if the curing is supported by increased temperature.

As set out above, a particular advantage of the method in accordance with the present invention is that it is universally applicable and in particular essentially not limited with regard to the kind and material of the substrate, with regard to the kind and composition of the ink and/or varnish, with regard to the printing process, with regard to the parameters used in the printing process, with regard to the curing method and with regard to the curing parameters. Thus, the method in accordance with the present invention is suitable for virtually all substrates, which may be printed with at least one at least partially cured ink and/or at least one at least partially cured varnish. Good examples are for instance obtained, when the substrate is selected from the group consisting of papers, cardboards, plastic foils, glass, nonwovens, fabrics, tissues, metal foils, metal sheets, and arbitrary combinations of two or more of the aforementioned substrates.

Likewise, to this, the method in accordance with the present invention is not particularly limited concerning the used ink and/or varnish. In particular, the method in accordance with the present invention is suitable for any ink/varnish, which may be printed onto a substrate (or onto a primer applied on a substrate) with a common printing process, such as with a printing process, which is selected from the group consisting of offset printing, flexographic printing, gravure printing, tampon printing, digital printing, inkjet printing, screen printing, intaglio printing, and arbitrary combinations of two or more of the aforementioned printing processes.

Particular good results are even obtained, when the at least one ink and/or varnish is an energy curing ink and/or varnish. With the prior art methods, it is a particular challenge to reliably determine the curing degree of such energy curing inks and varnishes. Preferred energy curing inks and varnishes are irradiation and/or electron beam curing inks and/or varnishes and more preferred are UV curing inks and/or varnishes.

Any energy curing ink and/or varnish, such as UV curing ink and/or varnish, includes a curing initiator, namely in the case of an UV curing ink and/or varnish, a photoinitiator. Suitable examples for curing initiators and particularly photoinitiators are in particular those, which may be spectroscopically quantified for example by means of an absorption measurement, an extinction/absorption measurement, a transmittance measurement or a fluorescence measurement at a suitable wavelength, such as between 250 and 400 nm. Accordingly, particularly preferred examples of photoinitiators are those being selected from the group consisting of benzophenones, $\alpha$-hydroxy ketones, $\alpha$-alkoxylketones, $\alpha$-aminoketones, aminoalkylphenones, acyl phosphine oxides, bisacylphosphinoxides, dialkylamines, thioxanthones, multifunctional amino benzoates, benzildimethylketals, phosphine oxides, 2-benzyl-2-dimethyl-amino-1-(4-morpholinophenyl)-butanone-1, 2-benzyl-2-dimethylamino-1-(4-morpholino-phenyl)-butanone-1, acetophenones, methylobenzoyl-benzoate, methylbenzoylformate, 2-methyl-1-(4-methylthiophenyl)-2-morpholinpropan-1-one, 2-ethyl-hexyl-4-dimethylaminobenzoate, ethyl-4-dimethylaminobenzoate, N-methyldi-ethanolamine, polymeric aminobenzoate derivatives, polymeric benzophenone derivatives, polymeric thioxanthone derivatives, camphorquinone, and arbitrary combinations of two or more of the aforementioned compounds. For cationic curing systems, blocked Lewis or Broensted acids, like bis-(($C_{10}$-$C_{14}$)-alkylphenyl)-iodoniumhexafluoro-antimonate, bis-(4,4-dodecylphenyl)-iodoniumhexafluorophosphate or bis-(4-methyl-phenyl)iodoniumhexafluoro-phosphate, are suitable.

Another important component of an energy curing ink and/or varnish is reactive monomer and/or oligomer with e.g. acrylic-, vinyl- or epoxy-functional groups. The at least partially cured energy curing ink and/or at least partially cured energy curing varnish may comprise at least one radically polymerizable monomer and/or at least one radically polymerizable oligomer, which is for example selected from the group consisting of acrylates, such as propoxylate (4) glycerol triacrylate, trimethylolpropantriacrylate, ethoxylated trimethylolpropane triacrylate, propoxylated trimethylolpropane triacrylate, pentaerythritol triacrylate, pentaerythritol(4)propoxylated-triacrylate, tri-functional monomers, such as Laromer types from BASF or Ebecryl 2047 or Ebecryl 12 from Allnex, di-trimethylolpropane tetraacrylate, pentyerythritol-tetraacrylate, ethoxylated pentaerythrioltetraacrylate, dipentaerythritol-pentaacrylate, dipentaerythritol hexaacrylate, oxiranes, and arbitrary combinations of two or more of the aforementioned substances.

In addition, the method in accordance with the present invention is also particularly suitable for at least one oxidatively curing ink and/or varnish.

Apart from possible curing initiators, reactive monomers and oligomers, the at least one ink and/or varnish used in the method in accordance with the present invention preferably comprises binder, solvent and/or additives. For instance, it may contain 5 to 90% by weight of binder. The present invention is not particularly limited concerning the kind of binder included in the ink and/or varnish. Suitable examples therefore are binders being selected from the group consisting of polyesters, polyethers, polyurethanes, polyamides, polyacrylates, maleinate resins, collophonium resins, ketone resins, alkyd resins, collophonium modified phenolic resins, hydrocarbon resins, silicates, silicones, silanes, phenolic resins, urea resins, melamine resins, polyterpene resins, polyvinylalcohols, polyvinylacetates, polyvinylchloride, polyvinylethers, polyvinylpropionates, polymethacrylates, polystyrenes, polyolefines, coumarone-indene resins, aromatic formaldehyde resins, carbamide acid resins, sulfonamide resins, chlorinated resins, nitrocellulose, CAB (cellulose acetate butyrate), CAP (cellulose acetate propionate), cellulose compounds, rubbers, radiation curing resins, and arbitrary combinations of two or more of the aforementioned binders. Suitable examples for solvents are those being selected from the group consisting of mineral oils, vegetable oils, fatty acid esters, alcohols, esters, ethers, glycols, water, aromatic compounds, water, monomers and oligomers with hydroxy, carboxy, alkoxy, amino functionality, and arbitrary combinations of two or more of the aforementioned solvents. Examples for additives are those being selected from the group consisting of rheological additives, adhesives, defoamers, slip additives, anti-corrosion additives, gloss additives, waxes, wetting agents, curing agents, chelating agents, photoinitiators, inhibitors, desiccants, stabilizers, emulsifiers, pH adjustment additives, abrasion resistance additives, plasticizers, antistatic additives, preservatives, light protection agents, matting agents and arbitrary combinations of two or more of the aforementioned additives.

Particularly suitable is at least one ink and/or varnish, which contains as binder acrylic functional polymers, oligomers and/or monomers, particularly in the case of energy curing inks or varnishes.

In accordance with a further development of the idea of the present invention it is suggested that the at least one ink and/or varnish is a two-component ink and/or varnish, which includes in one component at least one polyol compound, and in the other component at least one isocyanate compound.

Moreover, the at least one ink and/or varnish may be a two-component ink and/or varnish, which includes in one component at least one epoxy compound, and in the other component at least one amino-functional compound.

In accordance with the present invention, the at least one at least partially cured ink and/or varnish printed on the substrate comprises at least one extractable compound. An extractable compound is defined in accordance with the present invention as compound having a weight average molecular weight of at most 5,000 g/mol. In accordance with the present invention, the weight average molecular weight is measured with gel permeation chromatography using a polystyrene standard and a sample concentration of 50 to 70 mg in 10 ml tetrahydrofuran (THF), wherein the column temperature is 30° C., the temperature of the refractive index detector is 35° C. and the flow rate 1 ml/min. More preferably, the weight-average molecular weight of the extractable compound in the at least partially cured ink and/or varnish is at most 3,000 g/mol, more preferably of at most 2,000 g/mol, and most preferably of at most 1,000 g/mol.

Since in step c) a spectroscopic characteristic of the solvent extract including the extractable compound of the ink and/or varnish is determined, it is preferred that the at least one extractable compound absorbs or emits radiation at at least one wavelength between 190 and 4,000 nm, preferably between 190 and 3,000 nm, more preferably between 200 and 450 nm, and most preferably between 250 and 400 nm.

Also, it is preferred that the at least one extractable compound reacts with another component included in the solvent to a compound, which absorbs radiation at at least one wavelength between 190 and 4,000 nm, preferably between 190 and 3,000 nm, more preferably between 200 and 450 nm and most preferably between 250 and 400 nm.

For instance, the at least one extractable compound may be in the aforementioned embodiment an amine synergist, which reacts with copper ions to a compound, which absorbs radiation at at least one wavelength between 190 and 4,000 nm, preferably between 190 and 3,000 nm, more preferably between 200 and 450 nm, and most preferably between 250 and 400 nm. The addition of a copper salt to the extraction solution can enhance the extinction/absorption value e.g. of amine synergists or other compounds capable of forming a complex with copper ions.

In a further development of the idea of the present invention, it is proposed that in step b) one sample is cut from the printed substrate, wherein the sample has a surface of 0.01 to 100 cm$^2$, preferably of 0.1 to 50 cm$^2$, more preferably of 1 to 25 cm$^2$, and most preferably of 4 to 20 cm$^2$. This embodiment is particularly suitable for substrates, which are homogeneously printed with the at least one ink and/or varnish, respectively, i.e. in which the thickness of the at least one ink and/or varnish, respectively, is homogeneous over the whole surface of the substrate.

However, for substrates, which are inhomogeneously printed with the at least one ink and/or varnish, respectively, i.e. in which the thickness or coverage of the at least one ink and/or varnish, respectively, varies, it is preferred that in step b) two or more samples are cut from the printed substrate, wherein the samples have a total surface of 0.01 to 100 cm$^2$, preferably of 0.1 to 50 cm$^2$, more preferably of 1 to 25 cm$^2$, and most preferably of 4 to 20 cm$^2$. In this case, an average value is obtained from the different samples. In addition, the sample size should be adjusted in order to be able to measure in the linear range of the spectrophotometer used.

In accordance with a particularly preferred embodiment of the present invention, the at least one sample is cut in step b) from the most critical area of the printed substrate provided in step a), wherein the most critical area is defined as the area that resembles the highest calculated spectroscopic characteristic. Methods for the calculation of this area are listed further below.

The most critical area of the printed substrate may be determined for instance as follows:
i) Providing a pdf document of the pattern of the printed substrate provided in step a),
ii) evaluating the color combinations for each area of the pdf document,
ii) entering the data of the color combinations for each area into the empirical model so as to calculate for each area a reference value for the spectroscopic characteristic,
iii) determining the area having the highest reference value, and
iv) displaying the calculated area to the user.

The pdf document of the pattern of the printed substrate provided in step a) may be the template of the pattern, which is sent by the customer to the printer, or may be generated during the computer-to-plate (ctp) process.

Evaluating the color combinations for each area of the pdf document may be simply done by using a pdf reading program, such as Adobe Photoshop CC 2019, which allows for instance to display for each pixel or defined area of the pdf file the color combination, for example as its composition of the basis colors cyan (C), magenta (M), yellow (Y) and black (K) which corresponds to the ink coverage of these colors.

Just exemplarily, the following two specific methods are mentioned to determine the most critical area for a print job.

According to method 1, the print job is defined in a file in a pdf or CIP3 format. This pdf format can be analyzed e.g. via Adobe Photoshop CC 2019, Adobe InDesign CC 2019, Adobe Illustrator CC 2019, Adobe Acrobat Pro DC 2019, Esko ArtPro 18 or QuarkXpress 2018. The CIP3 files are created during the CTP workflow in order to process pdf files for the printing machine. Typical CIP3 workflow programs include Heidelberg Prinect 2019, Agfa Graphics Apogee 10, Fujifilm XMF workflow 6, Kodak Prinergy workflow 8.3, Esko Nexus 10, and Harlequin RIP 12. Single Pixels or even larger areas can be investigated for their composition in terms of CMYK inks. The composition resembles the ink coverage of each of these inks, for Yellow (Y), for Magenta (M), for Cyan (C), and for Black (K). The image can thus be analyzed on a raster basis, with overlapping rasters that are shifted, for example, 0.5 cm from each other. By knowing the area coverage, which means the ink coverage of each ink applied in all analyzed areas, and by entering all this information in the empirical model, one can determine the area with the highest calculated spectroscopic characteristic.

According to method 2, as a reference calibration curves of each ink of an ink series, e.g. Yellow, Magenta, Cyan, Black, are printed as a full tone or mixed with a transparent corresponding varnish. The varnish is composed of the same compounds as the ink but contains no pigment. The mixtures for the calibration curve may be composed of 1% ink plus 99% varnish, 5% ink plus 95% varnish, 10% ink plus 90% varnish up to 75% ink plus 25% varnish and so forth. The inks are printed with the same gram mage as was used for the design of experiments, and after curing the spectral curves or the spectral photometric data (Lab/LCh) are measured. By this means a calibration curve for the correlation of colored ink content (what equals ink coverage) and Lab/LCh values is obtained. The prints, e.g. of a print job, can be screened e.g. with a spectral photometer like e.g. X-Rite spectro-Eye. The obtained spectral values or curves can then be analyzed with e.g. an Ink Formulation Software, e.g. provided by X-Rite. Due to characteristic absorptions of the used inks and due to the intensity of the absorptions it can be calculated how much of each colored ink was applied on the respective area.

Any solvent may be used in step b) of the method in accordance with the present invention, in which the extractable compound has a sufficiently high solubility. Good results are particularly obtained, when at least one of the at least one extractable compound has at 23° C. a solubility in the solvent of at least 50 µg/l, preferably between 50 µg/l and 100 mg/l, more preferably between 500 µg/l and 20 mg/l, and most preferably between 1 mg/l and 10 mg/l.

Examples for suitable solvents are those, which are selected from the group consisting of alcohols, water, water-alcohol mixtures, ketones, esters, ethers, alkanes, cycloalkanes, aromatic solvents, tetrahydrofurane, dioxane, and arbitrary combinations of two or more of the aforementioned substances. Particularly suitable solvents are alcohols or water-alcohol mixtures, wherein the alcohol is preferably a $C_{1-10}$-alcohol, more preferably a $C_{1-6}$-alcohol, even more preferably a $C_{1-4}$-alcohol, and most preferably ethanol.

The solvent may contain a further component, such as copper ions reacting with the at least one extractable compound to a compound, which absorbs radiation at at least one wavelength between 190 and 4,000 nm, preferably between 190 and 3,000 nm, more preferably between 200 and 450 nm, and most preferably between 250 and 400 nm. This embodiment allows to enhance the extinction/absorption value e.g. of amine synergists or other compounds capable of forming a complex with copper ions.

Preferably, the sample is placed in step b) in a volume of solvent, which is at least 0.1 ml solvent per $cm^2$ sample, preferably 0.1 to 100 ml solvent per $cm^2$ sample, more preferably 0.25 to 20 ml solvent per $cm^2$ sample, even more preferably 0.4 to 10 ml solvent per $cm^2$ sample, and most preferably 0.5 to 5 ml solvent per $cm^2$ sample. This assures that enough solvent is present to extract necessary quantities of the extractable compounds within reasonable time. In addition, the amount of solvent should be adjusted in order to be able to measure in the linear range of the spectrophotometer used.

The present invention is not particularly limited concerning the time period, for which the sample is incubated in step b) in the solvent. Good results are e.g. obtained, when the sample is incubated in step b) for 30 seconds to 5 hours, preferably for 1 to 60 minutes, more preferably for 2 to 10 minutes, and most preferably for 4 to 6 minutes.

In order to allow the extractable compound(s) in step (b) to diffuse into the solvent without mechanically releasing the at least one cured ink and/or varnish, respectively, from the substrate, it is preferred that the incubation in step b) is performed without agitation of the solvent, in which the sample is placed, and at ambient temperature. Alternatively, the incubation in step b) may be performed with gently agitating the solvent. However, in the latter case care should be taken that the at least one cured ink and/or varnish, respectively, is not mechanically released from the substrate in this method step. In addition, slightly raised temperatures may also be used within the extraction step.

In a further development of the idea of the present invention, it is proposed that the spectroscopic characteristic of the solvent extract is measured in step c) at a wavelength, at which the numeric value of the spectroscopic characteristic is at least 50% of the peak maximum of the spectroscopic characteristic in the spectrum of the solvent extract, from which preferably the respective spectrum of the solvent has been subtracted. The subtraction of the respective spectrum of the solvent from the spectrum measured from the solvent extract in step c) assures that the measurement is not falsified by the spectroscopic characteristics of the solvent and that indeed any peak in the spectrum of the solvent extract is that of an extractable compound from the at least one ink and/or varnish, respectively, and not from the solvent.

In accordance with a particular preferred embodiment of the present invention, the spectroscopic characteristic, which is quantitatively measured in step c), is selected from the group consisting of extinction, transmittance, absorption, absorbance, fluorescence, and arbitrary combinations of two or more thereof.

More preferably, the spectroscopic characteristic, which is quantitatively measured in step c), is the extinction/absorption or transmittance of the solvent extract. Such extinction/absorption and transmittance measurements may be made in standard instruments available in most of the laboratories.

In the latter embodiment, it is preferred that the extinction/absorption or transmittance of the solvent extract is measured in step c) at a wavelength, at which the numeric value of the extinction/absorption or of transmittance is at least 50% of the peak maximum of the extinction/absorption or transmittance spectrum, from which the respective spectrum of the solvent has been subtracted. Again, the subtraction of the respective spectrum of the solvent from the spectrum measured in step c) assures that the measurement is not falsified by the spectroscopic characteristics of the solvent and that indeed any peak in the spectrum of the solvent extract is that of an extractable compound from the at least one ink and/or varnish, respectively, and not from the solvent.

Even more preferably, the extinction/absorption or transmittance of the solvent extract is measured in step c) at the wavelength of the peak maximum of the extinction/absorption or transmittance spectrum, from which the respective spectrum of the solvent has been subtracted.

Particularly preferred, the extinction/absorption of the solvent extract is quantitatively measured in step c) at at least one wavelength between 200 and 450 nm, and most preferably at at least one wavelength between 250 and 400 nm.

If two or more migratable compounds are included in the at least one ink and/or varnish, respectively, —such as in the case of at least one ink and/or varnish, respectively, which comprises two or more different photoinitiators—only one of these, some of these or all of these may be detected with the method in accordance with the present invention. For example, a mixture of photoinitiator, not reacted monomers and additives, which do not participate during the crosslinking, such as slip additives, may migrate into the solvent, from which then only the photoinitiator shall be quantitatively measured. If only one of the contained migratable compounds shall be detected, step c) is performed by using a wavelength, at which this compound absorbs or emits radiation. If some or all of the migratable compounds shall be detected, step c) may be performed by using one wavelength, at which all these compounds absorb or emit radiation. Alternatively, step c) may be performed by using two or more different wavelengths selected so that all these compounds absorb or emit radiation at at least one of these wavelengths.

Subsequently, the present invention is described by means of an illustrating, but not limiting examples.

Example 1

A method for controlling the curing degree of an at least partially cured ink printed on a substrate in accordance with the present invention was made by making use of a reference value having been obtained with an empirical model generated with the software Cornerstone 7.1.

In brief, a D-optimal design of experiments was generated and then the experiments suggested by the software were performed. The results of the experiments were entered into the software, which therefrom was calculated a second order model. Then a specific print order has been performed on a printing machine and the specific parameters of the printing method have been entered into the software, which calculated therefrom reference values for different areas of the printed substrate to be produced by the printing method. During the printing method a sample was cut out from a specific area of the printed substrate, incubated with a solvent so as to prepare a solvent extract, from which the extinction was measured. The measured extinction was then compared the reference value of the extinction for the same area of the printed substrate, which has been calculated by the software.

Generating the D-Optimal Design of Experiments and Performing the Experiments

It was decided to enter into the software as printing parameters to be varied the following parameters: The ink coverage, the color density, the kind of substrate, the lamp intensity, and thus the lamp dosage. The reason for varying these parameters were that they have a significant influence on the printing process, some might even alter during the printing method. For instance, the Lamp intensity—and as a consequence the lamp dosage—may vary during the life time of the lamp and the evaluation during this printing tests simulates lamp aging. Various kinds of substrates currently used on the market were selected, since the printer varies the substrate according to the print job. The ink coverage and composition were varied since printing jobs can be composed of various combinations of cyan (C), magenta (M), yellow (Y), and black (K) ink in different compositions and coverages. The color density might also vary since the printing machine might not be well adjusted, show inconsistencies during a printing job or drift over a longer time without recalibration.

More specifically, for generating the D-optimal design of experiments, the following parameters were entered into the software with following settings:

Ink series NewV Pack MGA, hubergroup Germany
Fount solution: 3.5% SUBSTIFIX AF 8319/09, Hubergroup Germany
Printing machine: KBA RA 106-6+L (Koenig und Bauer AG, Radebeul, Germany)
Machine calibration: ISO 12647-2 2013 (process standard offset)
UV lamp type: 2×200 Watt Hg-UV lamps (Koenig und Bauer AG, Radebeul, Germany)
Color density full tone, based on ISO machine calibration with ±0.2 deviation: 1.5±0.2 (C), 1.5±0.2 (M), 1.45±0.2 (Y), 1.8±0.2 (K) g/m$^2$
Grammage of each full tone ink: 1.0±0.2 (C), 1.1±0.2 (M), 1.1±0.2 (Y), 1.3±0.2 g/m$^2$
Substrate: Invercote G 220 g/m$^2$, Niklaselect 80 g/m$^2$
Printing speed: 13.000 sheets/hour
UV lamp intensity: varied in 5% steps
UV lamp dosage: 85, 100, 120 mJ/cm$^2$
Sample area: 20 cm$^2$
Solvent for extraction: ethanol
Extraction time: 5 min
UV-Spectrophotometer: Lambda II photometer (Perkin Elmer, Waltham, Mass., USA), resolution 1 nm, scan rate 240 nm/min, slit 2 nm
UV wavelength: 310 nm
UV cells: Rotilabo single-use UV cells, solvent resistant, Makro, 4.0 mL cuvettes (Carl Roth GmbH+Co. KG, Karlsruhe, Germany)

From these data, a d-optimal design of experiments was suggested by the software, which comprised 55 test fields to be printed. According to this proposed plan, the proposed full tone fields were printed with the given parameters and settings.

Firstly, each ink was printed separately on the substrate. Samples were cut out of different areas of each printed ink and the grammage for all areas was weighed with a suitable analytical balance. Then, the inks have been printed together one above another on the substrate and samples have been cut out. Each of these samples has been incubated separately with for 5 min in ethanol, wherein the ratio of ethanol to sample was adjusted to be within the linear measurement range of the UV/Vis spectrophotometer (Genesys 50, Thermo Fisher Scientific, Waltham, Mass., USA) of preferably 0.1 to 1 A.U. Thereafter, each sample has been removed from the solvent so as to obtain a solvent extract. From each solvent extract, the absorption at 310 nm was determined using a UV-Vis spectrophotometer. The absorption values were calculated for an ethanol volume of 10 mL for better comparability. The obtained results are shown in the following list, in which the analyzed fields with the corresponding settings and the measured extinction/absorption reference values including three additionally and manually entered center points to improve the error of the calculated model are given. Since the absorption values were calculated for an ethanol volume of 10 mL, in the list measure absorption values above 1.0 A.U. can be found.

All in all, for each sample the grammage, the ink coverage of each ink as well as the spectroscopic characteristic was determined.

| Ink coverage K/% | Ink coverage C/% | Ink coverage M/% | Ink coverage Y/% | Color density/grammage deviation | Substrate | Lamp intensity | Measured absorption value/A.U. |
|---|---|---|---|---|---|---|---|
| 40 | 40 | 60 | 20 | −0.20 | Niklaselect | 50 | 0.389 |
| 60 | 60 | 100 | 80 | −0.20 | Niklaselect | 50 | 0.647 |
| 0 | 20 | 80 | 80 | −0.20 | Invercote G | 100 | 0.237 |
| 20 | 60 | 100 | 20 | −0.20 | Invercote G | 100 | 0.188 |
| 80 | 60 | 20 | 100 | −0.20 | Invercote G | 50 | 0.492 |

| Ink coverage K/% | Ink coverage C/% | Ink coverage M/% | Ink coverage Y/% | Color density/ grammage deviation | Substrate | Lamp intensity | Measured absorption value/A.U. |
|---|---|---|---|---|---|---|---|
| 0 | 100 | 20 | 100 | −0.20 | Niklaselect | 50 | 0.528 |
| 100 | 100 | 100 | 0 | −0.20 | Invercote G | 50 | 0.482 |
| 80 | 20 | 0 | 20 | −0.20 | Invercote G | 75 | 0.22 |
| 0 | 0 | 0 | 100 | −0.20 | Niklaselect | 100 | 0.253 |
| 0 | 100 | 0 | 100 | −0.20 | Invercote G | 100 | 0.253 |
| 40 | 0 | 40 | 40 | −0.20 | Invercote G | 100 | 0.193 |
| 100 | 0 | 0 | 100 | −0.20 | Niklaselect | 50 | 0.594 |
| 20 | 80 | 40 | 60 | −0.20 | Niklaselect | 75 | 0.461 |
| 100 | 100 | 0 | 0 | −0.20 | Niklaselect | 100 | 0.306 |
| 0 | 0 | 20 | 0 | −0.20 | Invercote G | 50 | 0.043 |
| 100 | 0 | 100 | 0 | −0.20 | Niklaselect | 100 | 0.298 |
| 0 | 0 | 100 | 100 | −0.20 | Invercote G | 50 | 0.461 |
| 40 | 100 | 100 | 100 | −0.20 | Niklaselect | 100 | 0.481 |
| 100 | 80 | 60 | 100 | −0.20 | Invercote G | 100 | 0.264 |
| 80 | 0 | 80 | 80 | 0 | Niklaselect | 100 | 0.471 |
| 100 | 20 | 20 | 60 | 0 | Invercote G | 100 | 0.22 |
| 100 | 100 | 60 | 80 | 0 | Invercote G | 75 | 0.373 |
| 20 | 0 | 60 | 40 | 0 | Invercote G | 50 | 0.303 |
| 0 | 80 | 80 | 60 | 0 | Niklaselect | 50 | 0.593 |
| 0 | 40 | 0 | 0 | 0 | Invercote G | 100 | 0.069 |
| 40 | 80 | 0 | 80 | 0 | Invercote G | 50 | 0.483 |
| 60 | 20 | 40 | 0 | 0 | Niklaselect | 50 | 0.384 |
| 0 | 100 | 100 | 100 | +0.20 | Invercote G | 50 | 0.875 |
| 0 | 80 | 20 | 20 | +0.20 | Invercote G | 100 | 0.192 |
| 80 | 100 | 100 | 60 | +0.20 | Invercote G | 100 | 0.308 |
| 60 | 40 | 20 | 40 | +0.20 | Niklaselect | 75 | 0.492 |
| 0 | 0 | 100 | 100 | +0.20 | Niklaselect | 50 | 1.054 |
| 100 | 100 | 0 | 0 | +0.20 | Invercote G | 50 | 0.521 |
| 20 | 40 | 100 | 80 | +0.20 | Niklaselect | 50 | 1.132 |
| 60 | 0 | 60 | 60 | +0.20 | Niklaselect | 100 | 0.478 |
| 100 | 100 | 0 | 100 | +0.20 | Niklaselect | 50 | 1.316 |
| 0 | 100 | 0 | 0 | +0.20 | Niklaselect | 50 | 0.401 |
| 100 | 100 | 100 | 0 | +0.20 | Niklaselect | 50 | 0.844 |
| 80 | 80 | 60 | 0 | +0.20 | Invercote G | 100 | 0.223 |
| 100 | 0 | 0 | 100 | +0.20 | Invercote G | 100 | 0.317 |
| 0 | 100 | 100 | 0 | +0.20 | Niklaselect | 100 | 0.402 |
| 100 | 40 | 40 | 20 | +0.20 | Niklaselect | 100 | 0.409 |
| 100 | 0 | 0 | 0 | +0.20 | Niklaselect | 50 | 0.535 |
| 100 | 0 | 100 | 100 | +0.20 | Invercote G | 50 | 0.795 |
| 100 | 20 | 100 | 40 | +0.20 | Niklaselect | 100 | 0.596 |
| 60 | 100 | 80 | 100 | +0.20 | Invercote G | 100 | 0.407 |
| 0 | 0 | 100 | 0 | +0.20 | Invercote G | 50 | 0.328 |
| 0 | 100 | 0 | 100 | +0.20 | Niklaselect | 100 | 0.612 |
| 20 | 0 | 0 | 0 | +0.20 | Niklaselect | 100 | 0.077 |
| 0 | 0 | 0 | 100 | +0.20 | Invercote G | 50 | 0.446 |
| 0 | 100 | 100 | 100 | +0.20 | Invercote G | 100 | 0.427 |
| 40 | 60 | 80 | 0 | +0.20 | Invercote G | 75 | 0.371 |
| 40 | 40 | 40 | 60 | 0 | Invercote G | 75 | 0.324 |
| 40 | 40 | 40 | 60 | 0 | Invercote G | 75 | 0.333 |
| 40 | 40 | 40 | 60 | 0 | Invercote G | 75 | 0.301 |

Generating the Empirical Model of Second Order

The experimental data obtained in the aforementioned experiments were entered into the software, which calculated therefrom the coefficients of an empirical model of second order. Any of these coefficients describes the degree of influence of the respective parameter to the measured spectroscopic characteristic, i.e. in this case the extinction/absorption at 310 nm.

The calculated coefficients for the different parameters/terms resulting in the square root of the extinction/absorption as a response are shown in the following table.

| Term | Coefficient |
|---|---|
| Constant | 4.3E−01 |
| K | 4.1E−03 |
| C | 3.4E−03 |
| M | 2.0E−03 |
| Y | 3.5E−03 |
| Color density | 6.5E−03 |
| Substrate: | |
| Invercote G | −3.7E−02 |
| Niklaselect | 3.7E−02 |
| Intensity lamp | −2.8E−03 |
| C * K | −1.5E−05 |
| K * M | −7.0E−06 |
| K * Y | −2.1E−05 |
| Color density * K | −1.9E−05 |
| Intensity lamp * K | −1.2E−05 |
| C^2 | −1.1E−05 |
| C * M | −7.5E−06 |
| C * Y | −1.0E−05 |
| Color density * M | 1.3E−05 |

-continued

| Term | Coefficient |
|---|---|
| Substrate * Y: | |
| Invercote G | −3.4E−04 |
| Niklaselect | 3.4E−04 |
| Color density * Substrate: | |
| Invercote G | −7.0E−04 |
| Niklaselect | 7.0E−04 |
| Color density * Intensity lamp | −4.0E−05 |

The final model allows predictions for the relevant range of parameters.

$$\eta = \beta_0 + \sum_{i=1}^{n} \beta_i \cdot x_i + \sum_{i \leq j}^{n} \sum_{j}^{n} \beta_{ij} \cdot x_i \cdot x_j$$

in which
$\eta$=response, which is here the square root of the extinction/absorption
$\beta_0$, $\beta_i$, $\beta_{ij}$=coefficients
$x_i$, $x_j$=settings of the different factors, e.g. 75 for a lamp intensity of 75%

The response was fitted to a function of second order by means of a least squares fit.

By using the obtained empirical model, one reference value for every combination of the varied parameters can be obtained.

Controlling the Curing Degree of an at Least Partially Cured Ink During a Printing Process:

The obtained empirical model of example 1 was then applied to a real printing job. A printer printed a full tone printing job with a sheet-fed offset printing machine with UV lamps with the following parameters:

Ink series NewV Pack MGA, hubergroup Germany
Fount solution: 3.5% SUBSTIFIX AF 831909, Hubergroup Germany
Printing machine: KBA RA 106-6+L (Koenig und Bauer AG, Radebeul, Germany)
Machine calibration: ISO 12647-2 2013 (process standard offset)
UV lamp type: 2×200 Watt Hg-UV lamps (Koenig und Bauer AG, Radebeul, Germany)
Printing speed: 13.000 sheets/hour
Sample area: 20 cm$^2$
Solvent for extraction: ethanol
Extraction time: 5 min
UV-Spectrophotometer: Lambda II photometer (Perkin Elmer, Waltham, Mass., USA), resolution 1 nm, scan rate 240 nm/min, slit 2 nm
UV wavelength: 310 nm
UV cells: Rotilabo single-use UV cells, solvent resistant, Makro, 4.0 mL cuvettes (Carl Roth GmbH+Co. KG, Karlsruhe, Germany)

The following settings of the above varied parameters were entered into the software, which used them to calculate the reference values for each area of the pattern of the printed substrate to be produced with the printing job in the empirical model obtained as described above:

Ink coverage: 50 (C), 50 (M), 20 (Y), and 60% (K)
Color density full tone: 1.4 (C), 1.45 (M), 1.35 (Y), 1.7 (K) g/m$^2$
Grammage of each full tone ink: 0.9 (C), 1.0 (M), 0.95 (Y), 1.2 (K) g/m$^2$
Substrate: Invercote G 220 g/m$^2$
UV lamp intensity: 75%
UV lamp dosage: 100 mJ/cm$^2$ Based on these data the software calculated a reference value of 0.29 A.U.

The printer has cut a sample from an area of the printed substrate, prepared therefrom a solvent extract and measured then the extinction thereof as described above for the experiments made for generating the empirical model. The absorption obtained by the printer was 0.31 A.U. This value was entered into the software. The software then compared the measured value with the reference value. The measured extinction value was 7% higher than the reference value, showing that the curing degree was too low, since a higher extinction value means that more extractable compounds have been migrated into the solvent during the solvent extract preparation.

As a consequence thereof, the software suggested to increase the lamp intensity by +5% in order to increase the curing degree.

Example 2

This example was performed according to example 1 except that the following parameters were used.

Extraction of printed inks with $CuCl_2$ dissolved in ethanol
Ink series: NewV Set HS, Hubergroup, Deutschland
Printing machine: Prüfbau Printing proof machine (Prüfbau, Peißenberg, Germany)
Ink grammage: 2 g/m$^2$
Substrate: Invercote T (220 g/m$^2$)
UV lamp: Fe-doped HUV lamp
UV lamp dosage: 0.03, 0.04, 0.08, 0.33 J/cm$^2$
Machine speed: 10, 35, 60, and 85 m/min
Sample size: 4 cm$^2$
Copper(II) chloride concentration: 50 mg/L in ethanol
Extraction time: 5 min
UV-Spectrophotometer: Lambda II photometer (Perkin Elmer, Waltham, Mass., USA), resolution 1 nm, scan rate 240 nm/min, slit 2 nm
UV wavelength: 355 nm
UV cells: Rotilabo single-use UV cells, solvent resistant, Makro, 4.0 mL cuvettes (Carl Roth GmbH+Co. KG, Karlsruhe, Germany)

Here, samples were printed and cured using the above mentioned conditions. The sample area was cut out and extracted using a copper(II) chloride containing solvent. The extinction/absorption was measured. The results are shown in the FIGURE.

The FIGURE shows a comparison of the results of the sample extraction in $CuCl_2$ solution (line) to ethanol (line) shows significantly higher results for $CuCl_2$. As the extinction/absorption value of the pure $CuCl_2$ 0.01 A.U. was measured (line).

It can be seen that the extraction in $CuCl_2$ solution (line) is not a simple addition of the pure $CuCl_2$ and the sample in ethanol signals, but that the addition of $CuCl_2$ to the extraction solution of the sample enhances the resulting signal at 355 nm.

The invention claimed is:
1. A method for controlling a curing degree of at least one at least partially cured ink and/or varnish printed on a substrate, which comprises the following steps:
a) providing a substrate, which is printed with the at least one at least partially cured ink and/or at least partially cured varnish, wherein the at least one at least partially cured ink and/or at least partially cured varnish comprises at least one extractable compound, b) cutting at least one sample from an area of the printed substrate provided in step a), placing the at least one sample in a solvent, in which at least one of the at least one extractable compound is soluble, incubating the solvent with the at least one sample placed therein for at least 10 seconds and removing the at least one sample from the solvent to obtain a solvent extract, c) quantitatively measuring a spectroscopic characteristic of the solvent extract at at least one wavelength between 190 and 4,000 nm, at which at least one of the at least one extractable compound absorbs or emits radiation, so as to obtain a measured numeric value of the spectroscopic characteristic, d) comparing the measured numeric value of the spectroscopic characteristic measured in step c) with a reference value of the spectroscopic characteristic for the same area of the printed substrate, from which the at least one sample has been cut out in step b), and e) outputting a result, wherein the reference value of the spectroscopic characteristic for the same area of the printed substrate, from which the at least one sample has been cut out in step b), has been obtained by the use of an empirical model.

2. The method in accordance with claim 1, wherein the empirical model used for obtaining the reference value of the spectroscopic characteristic for the same area of the printed substrate, from which the at least one sample has been cut out in step b) is selected from the group consisting of linear models, second order models, and higher order models, wherein the empirical model has been obtained by making use of a design of experiments, which is selected from the group consisting of optimal designs of experiments, full factorial designs of experiments, fractional factorial designs of experiments, centrally composed experimental designs, and combinations thereof.

3. The method in accordance with claim 1, wherein the empirical model used for obtaining the reference value of the spectroscopic characteristic for the same area of the printed substrate, from which the at least one sample has been cut out in step b) is a second order empirical model obtained by making use of the results of a D-optimal design of experiments.

4. The method in accordance with claim 1, wherein the empirical model has been obtained by making use of the results of a plurality of experiments, in which the spectroscopic characteristic measured in step c) has been measured for an area of a printed substrate, wherein the plurality of experiments has been made by printing at least one ink and/or varnish onto the substrate, wherein one or more printing parameters have been varied in the individual experiments, wherein at least one of the one or more parameters that has been varied in the individual experiments is selected from the group consisting of ink coverage of each ink, gram mage of each ink, density of each ink, type of substrate, printing speed, UV lamp type, UV lamp intensity, UV lamp dosage, extraction time, and arbitrary combinations of two or more of the aforementioned parameters.

5. The method in accordance with claim 1, wherein substrate provided in step a) has been printed using a printing process having parameters selected from the group consisting of ink coverage of each ink, gram mage of each ink, density of each ink, type of substrate, printing speed, UV lamp type, UV lamp intensity, UV lamp dosage, and extraction time and the reference value of the spectroscopic characteristic for the same area of the printed substrate, from which the at least one sample has been cut out in step b), has been obtained by the use of a second order empirical model obtained by making use of the results of a D-optimal design of experiments, wherein in the D-optimal design of experiments at least one of the parameters used in the printing process used to provide the substrate according to step a) has been varied relative to the parameter used for printing the substrate provided in step a).

6. The method in accordance with claim 1, wherein the method is performed during a printing process, wherein the result being output in step e) is that:

i) the curing degree is sufficient, if the difference between the numeric value of the spectroscopic characteristic measured in step c) and the respective reference value is between a predetermined lower and an upper threshold, so that no amendment of the printing process is necessary, ii) the curing degree is too low, if the difference between the numeric value of the spectroscopic characteristic measured in step c) from the respective reference value is less than a predetermined lower threshold, so that an amendment of the printing process is necessary, or iii) the curing degree is higher than necessary, if the difference between the numeric value of the spectroscopic characteristic measured in step c) from the respective reference value is more than a predetermined higher threshold, so that an amendment is advisable.

7. The method in accordance with claim 6, wherein, when the result being output in step e) is that the curing degree is too low, in step e) an information is given, wherein the information comprises at least one of:

i) displaying the extent of how much a machine speed has to be reduced, if the printing process is a continuous process or a semi-continuous process, and/or ii) displaying the extent of how much a lamp power for curing the at least one printing ink and/or varnish has to be increased, if the curing is supported by irradiation, and/or iii) displaying a number of additional lamps being necessary for curing the at least one printing ink and/or varnish, if the curing is supported by irradiation, and/or iv) displaying the extent of how much a temperature during the curing has to be increased, if the curing is supported by temperature.

8. The method in accordance with claim 6, wherein, when the result being output in step e) is that the curing degree is higher than necessary, in step e) an information is given, wherein the information comprises at least one of:

i) displaying the extent of how much a machine speed has to be increased, if the printing process is a continuous process or a semi-continuous process, and/or ii) displaying the extent of how much a lamp power for curing the at least one printing ink and/or varnish has to be reduced, if the curing is supported by irradiation, and/or iii) displaying a number of lamps, which have to be switched off, if the curing is supported by irradiation, and/or iv) displaying the extent of how much a temperature during the curing has to be reduced, if the curing is supported by increased temperature.

9. The method in accordance with claim 1, wherein the at least one ink and/or varnish is an energy curing ink and/or varnish.

10. The method in accordance with claim 1, wherein the at least one extractable compound has a weight average molecular weight of at most 5,000 g/mol.

11. The method in accordance with claim 1, wherein the at least one extractable compound absorbs or emits radiation at at least one wavelength between 190 and 4,000 nm.

12. The method in accordance with claim 1, wherein the at least one extractable compound reacts with another component included in the solvent to a compound, which absorbs radiation at at least one wavelength between 190 and 4,000 nm.

13. The method in accordance with claim 1, wherein the printed substrate provided in step a) has a total area having multiple calculated spectroscopic characteristics which vary within the total area of the printed substrate provided in step a), wherein the calculated spectroscopic characteristics vary from a lowest calculated spectroscopic characteristic within the total area to a highest calculated spectroscopic characteristic within the total area and the at least one sample is cut in step b) from a most critical area of the printed substrate provided in step a), wherein the most critical area is an area within the total area of the printed substrate provided in step a) which has the highest calculated spectroscopic characteristic.

14. The method in accordance with claim 1, wherein the at least one extractable compound has a solubility in the solvent used in step b) at 23° C. of at least 50 µg/l.

* * * * *